United States Patent [19]

Rienmueller et al.

[11] Patent Number: 5,067,494
[45] Date of Patent: Nov. 26, 1991

[54] DEVICE FOR GENERATING TRIGGER SIGNALS FOR A MEDICAL APPARATUS DEPENDENT ON THE RESPIRATORY ACTIVITY OF A PATIENT

[75] Inventors: Rainer Rienmueller, Munich; Willi Kalender, Kleinseebach; Wolfgang Seissler, Uttenreuth Weiher, all of Fed. Rep. of Germany

[73] Assignee: Siemens Aktiengesellschaft, Munich, Fed. Rep. of Germany

[21] Appl. No.: 445,414

[22] Filed: Dec. 4, 1989

[30] Foreign Application Priority Data

Jan. 12, 1989 [EP] European Pat. Off. ........ 89100472.3

[51] Int. Cl.$^5$ ................................ A61B 6/03
[52] U.S. Cl. ............................ 128/653.1; 128/726; 378/8
[58] Field of Search .......... 128/653, 725, 726, 24 EL; 73/861.42, 861.52, 861.61; 378/8

[56] References Cited

U.S. PATENT DOCUMENTS

| | | | |
|---|---|---|---|
| 966,050 | 8/1910 | Ramage | 128/726 |
| 3,508,539 | 4/1970 | Mahoney | 128/727 |
| 3,524,058 | 8/1970 | Robertson et al. | 378/95 |
| 3,871,360 | 3/1975 | Van Horn et al. | 128/671 |
| 3,993,995 | 11/1976 | Kaplan et al. | 128/653 R |
| 4,005,311 | 1/1977 | Ledley | 378/8 |
| 4,441,505 | 4/1984 | Edwards et al. | 128/726 |
| 4,640,293 | 2/1987 | Garbe | 128/716 |
| 4,685,461 | 8/1987 | Forssmann et al. | 128/328 |
| 4,779,620 | 10/1988 | Zimmermann et al. | 128/653 A |
| 4,860,765 | 8/1989 | Hudimac | 128/725 |
| 4,930,508 | 6/1990 | Shimoni et al. | 128/653 A |
| 4,939,757 | 7/1990 | Nambu | 378/8 |

Primary Examiner—William E. Kamm
Assistant Examiner—Kevin Pontius

[57] ABSTRACT

A device for generating trigger signals for a medical apparatus, used for diagnosis and/or therapy, based on the respiratory activity of a patient includes a spirometer with a measurement transducer disposed therein for measuring respiratory air of a patient, and a signal generator connected to the transducer for generating trigger signals based on the respiratory measurement. A closure device can be provided in the spirometer in the respiratory path, which can be closed so that the flow respiratory air is briefly interrupted when a predetermined set value, for example obtained from the measured value, is reached.

1 Claim, 1 Drawing Sheet

DEVICE FOR GENERATING TRIGGER SIGNALS FOR A MEDICAL APPARATUS DEPENDENT ON THE RESPIRATORY ACTIVITY OF A PATIENT

BACKGROUND OF THE INVENTION

1. Field of the Invention

The present invention is directed to a device for generating signals dependent on the respiratory activity of a patient, and in particular to such a device adapted for generating trigger signals for a medical diagnosis and-/or therapy apparatus.

2. Description of the Prior Art

Body organs and anatomical structures are considerably displaced dependent on the respiratory activity of a patient. It is therefore necessary, for satisfactory results, in many medical examination and therapy methods, to synchronize the operation of the examination or therapy equipment with the respiration cycle of the patient. For example, individual measurements can be triggered when a defined respiratory condition is reached. For example, in computer tomography devices, such synchronization is needed for the creation of dynamic computer tomograms, wherein a chronological succession of identical anatomical structures is to be acquired at each measurement event. Data sets for three-dimensional or multi-planar reconstructions in computer tomography should also frequently be synchronized with the patient's respiration. In these types of measurements, tomograms of an organ or organs are taken at precisely defined spacings in chronologically successive measurements. The respiratory condition of the patient must be reproduced for each individual measurement, so that organ dislocations due to the respiration activity do not appear in the successive measurements. Similar requirements are present, for example, in magnetic resonance imaging and in lithotripsy, wherein a shock wave for disintegrating a calculus is triggered dependent on the patient's respiratory condition.

In addition to being capable of identifying any point (i.e., respiratory condition) within a patient's respiratory cycle, it is also desireable to define a respiratory condition in terms of absolute values. This is of significance, for example, in pulmonary density measurements. It is known to generate electrical signals corresponding to the respiratory condition of a patient by the use of a breathing belt which is tightened around the chest or stomach of a patient, and which generates electrical signals based on the expansion and contraction of the belt which occurs as the patient breathes. This is not a satisfactory solution, because no absolute measurement of the respiratory volumes is possible using this known device, and errors in whatever medical measurement or treatment is being undertaken dependent on the patient's respiratory activity may arise dependent on characteristics which vary from patient to patient, such as the degree to which the patient uses chest or diaphragm respiration.

SUMMARY OF THE INVENTION

It is an object of the present invention to provide a device for generating trigger signals dependent on the respiratory activity of a patient, adapted for use in controlling the operation of a medical diagnosis and/or therapy apparatus, which can also precisely measure the respiratory volume of the patient with small error.

The above object is achieved in accordance with the principles of the present invention in a device which includes a spirometer adapted to be traversed by the respiratory air of a patient, and which has a signal generator for generating the trigger signals dependent upon the flow of breath through the spirometer. The patient breathes through the spirometer via mouth piece for the entire duration of the examination or therapy. This is possible without problem in both open and closed systems. An exact acquisition of the vital capacity of the patient is possible using the spirometer. The particular type of respiration (i.e., chest or diaphragm respiration) of the patient has no influence on the generated signals.

In one embodiment, the spirometer may include a closure device for the respiratory tract, which is controlled such that the flow of breath is briefly interrupted when a predetermined set value is reached. When the closure device is closed, and thus the breathing is momentarily interrupted, it is assured that substantially no dislocation of organs or of anatomical structures ensues during a measurement or a therapy procedure.

DESCRIPTION OF THE PREFERRED EMBODIMENTS

Figure 1:
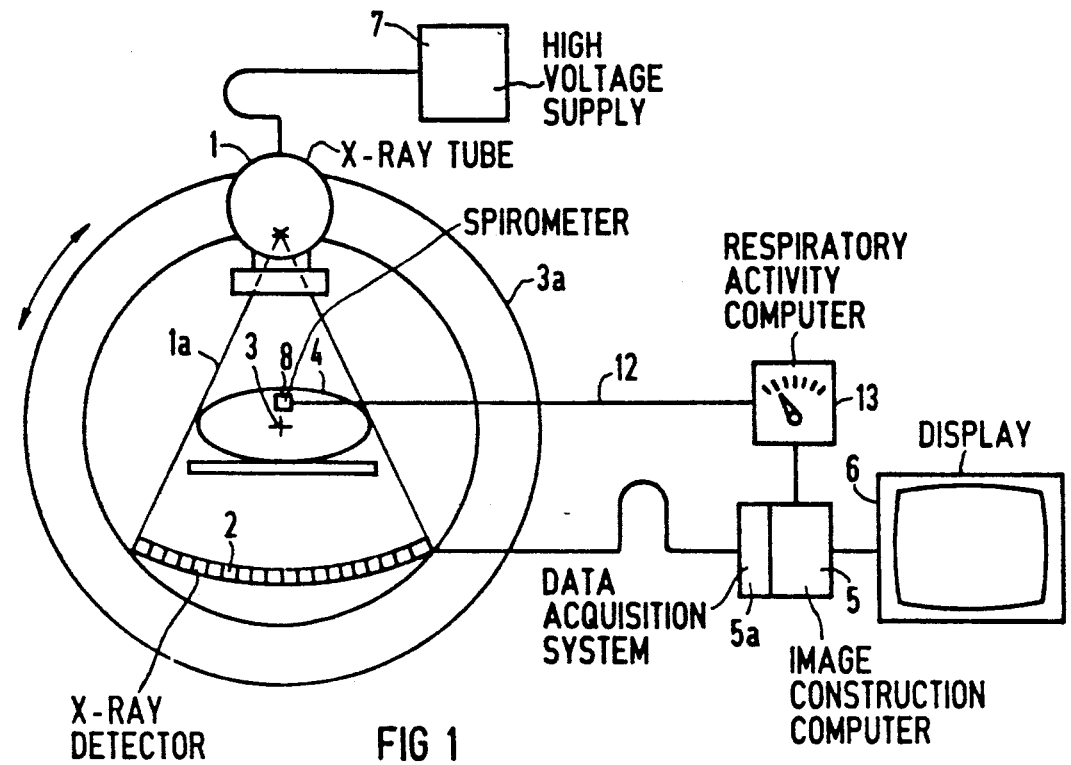
FIG. 1 is a schematic block diagram of a computer tomography apparatus of the type in which the device disclosed herein can be used.

A typical computer tomography apparatus, of the type in which a device for generating trigger signals based on the respiratory activity of the patient, as disclosed below, can be used is shown in FIG. 1. The computer tomography apparatus includes an x-ray tube 1, fed by a high voltage supply 7, which generates a fan-shaped x-ray beam 1a which irradiates a patient 4. Radiation attenuated by the patient 4 is incident on a radiation detector 2 consisting of over one hundred, for example 512, individual detectors arranged in a row. The fan-shaped x-ray beam 1a has a cross-sectional extent perpendicular to the slice plane, which is equal to the thickness of the slice. The x-ray beam 1a has an extent in the slice plane so that the entire cross-section of the patient 4 is penetrated by radiation.

The radiation detector 2 is curved around the focus of the x-ray tube 1. The x-ray tube 1 and the radiation detector 2 are mounted on a rotatable live frame 3a, so that the x-ray tube 1 and the radiation detector 2 are simultaneously rotated around an axis 3, which approximately coincides with the longitudinal axis of the patient 4. The number of detector elements in the radiation detector 2 is selected in accordance with the desired image resolution, so that the attenuation values of a picture element matrix of the irradiated transverse slice of the patient 4 can be calculated by a computer 5 on the basis of the aforementioned rotation. The image can then be reproduced on a display 6.

Each detector element of the radiation detector 2 has a measuring channel associated therewith which leads to the computer 5. Amplifier circuits, multiplexers and analog-to-digital converters, which in combination form a data acquisition system 5a, are provided in each measuring channel in a known manner.

Figure 2:
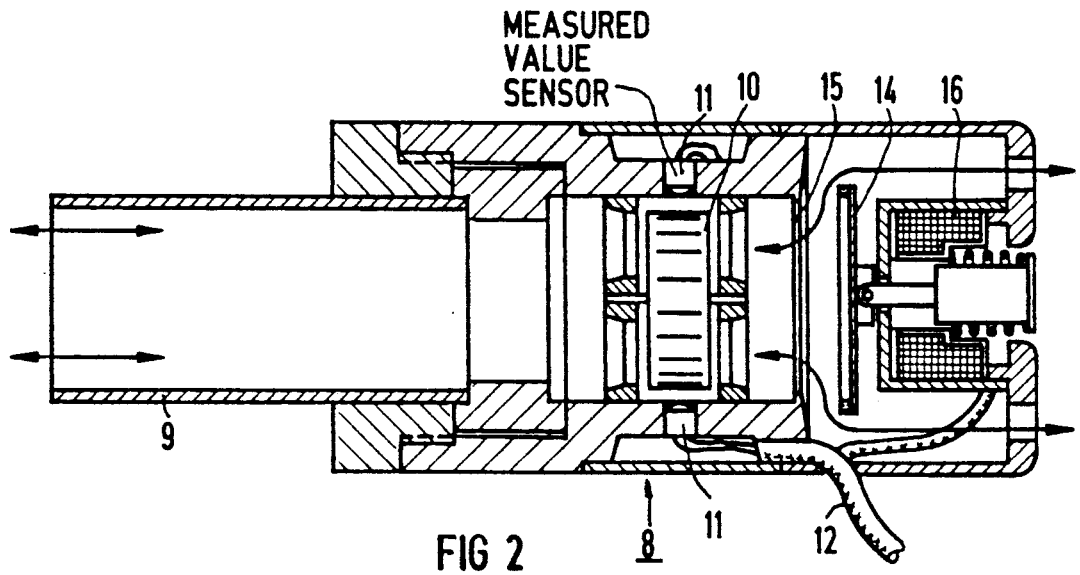
FIG. 2 is a side sectional view of a device for generating respiratory signals constructed in accordance with the principles of the present invention.

For acquiring signals identifying the respiratory activity of the patient 4, and for synchronization of the formation of the measured values with the respiratory activity, the patient 4 breathes through a spirometer 8 as shown generally in FIG. 1 and shown in greater detail in FIG. 2. The spirometer 8 has a mouthpiece 9 and a turbine 10 in the interior thereof, which is traversed by the flow of respiratory air from the patient. The respiratory air causes the turbine 10 to rotate. The turbine 10 is disposed in the field of view of measured value sensors 11. The measured value sensors 11 may, for example, be a part of an opto-electronic measuring system, with the rotation of the turbine 10 causing successive interruptions of a light path. The signals from the measured value sensors 11 are supplied to a respiratory activity computer 13 via a line 12.

The vital capacity of the patient 4 can be acquired with the spirometer 8, and stored in the respiratory activity computer 13. The physician or attendant can select a trigger threshold via the respiratory activity computer 13 as a percentage of the vital capacity, or in liters above the residual capacity, at which the acquisition of the measured respiratory value ensues. After the measurement has been enabled by the physician or attendant, the computer 13 compares the measured respiratory volume to the prescribed rated value, and supplies a trigger signal to the computer 5, i.e., to the imaging system, when the rated value is reached. This signal can also be used in the computer 5 to mark respiratory activity within the scan data.

It is desireable that the respiratory flow be mechanically interrupted simultaneously with the attainment of the rated value, so that the generation of the measured value can be undertaken at a fixed respiratory condition for a duration of a few seconds. For this purpose, the spirometer 8 has a closure plate 14 moveable in a longitudinal direction within the spirometer 8. The position of the closure plate 14 along the longitudinal direction is controlled by a magnetic coil 16. The closure plate 14 is shown in its open position in FIG. 2, so that the flow of respiratory air through the spirometer is unimpeded. When the magnetic coil 16 is activated, the closure plate 14 moves in the longitudinal direction to close an opening 15 in the spirometer 8, thus momentarily interrupting the respiratory activity of the patient so that the therapy, or acquisition of a measured value which will contribute to the image of the patient, is completed. Upon the completion of the therapy or measuring event, the respiratory path is again opened. It can be assured through a suitable timer or signal sampling device that the respiratory path, for safety reasons, is always opened again after a few seconds.

When possible, the patient 4 may hold the spirometer 8 himself, and may thus actively interrupt the examination at any time if shortness of breath occurs. The brief interruption of the respiratory flow therefore does not present a risk to the patient.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical diagnostic apparatus comprising:

a spirometer having a channel therein adapted to be traversed by the respiratory air of a patient, a turbine having a plurality of blades and being rotatably mounted in said channel so as to be rotated by respiratory air;

opto-electrical transducer means disposed in said spirometer and having a light path modulatable by rotation of said turbine blades for generating an electrical signal at a point in the respiratory cycle of the patient dependent on the rotation of said turbine and thus on the flow of respiratory air in said channel;

first computer means to which said electrical signal is supplied for generating a trigger signal at said point in the respiratory cycle and including means for setting a respiratory trigger threshold to select said point in said respiratory cycle;

a computer tomography imaging system connected to said first computer means, said computer tomography imaging system including means for conducting a scan of a patient consisting of a plurality of exposures of said patient respectively triggered by said trigger signal and for generating scan data during each exposure, and also including second computer means for constructing an image of the scanned region of said patient from said scan data, said first computer means including means for generating and supplying a signal to said second computer means in said computer tomography imaging system for marking respiratory activity at said point in said respiratory cycle within said scan data; and said spirometer also including means disposed in said channel connected to and operable by said first computer means for completely blocking inspiration and expiration in said channel when said respiratory trigger threshold is reached.

* * * * *